(12) United States Patent
Mihaylov et al.

(10) Patent No.: US 6,655,577 B2
(45) Date of Patent: Dec. 2, 2003

(54) SANITIZING SECURE AND SAFE MAIL BOX

(76) Inventors: Gueorgui Mihaylov, 1745 Lake Christopher Dr., Virginia Beach, VA (US) 23464; Evdokia Mihaylov, 1745 Lake Christopher Dr., Virginia Beach, VA (US) 23464

( * ) Notice: Subject to any disclaimer, the term of this patent is extended or adjusted under 35 U.S.C. 154(b) by 0 days.

(21) Appl. No.: 10/094,839

(22) Filed: Mar. 11, 2002

(65) Prior Publication Data

US 2003/0168507 A1 Sep. 11, 2003

(51) Int. Cl.[7] .............................................. B65G 11/04
(52) U.S. Cl. ......................... 232/45; 232/17; 232/35; 232/47; 422/24; 422/186.3
(58) Field of Search ............................ 232/45, 17, 47, 232/52, 34, 35; 422/24, 186.3; 34/275; 250/455.11, 492.1; 340/569; 116/202

(56) References Cited

U.S. PATENT DOCUMENTS

| | | | | |
|---|---|---|---|---|
| 1,432,843 A | * | 10/1922 | Dooley | 232/21 |
| 1,508,801 A | * | 9/1924 | Miller | 232/24 |
| 3,874,583 A | * | 4/1975 | Moll | 232/17 |
| 3,885,668 A | * | 5/1975 | McClain | 312/240 |
| 5,445,317 A | * | 8/1995 | Sokolowski | 232/34 |
| 5,526,979 A | * | 6/1996 | Mann | 232/33 |
| 5,979,751 A | * | 11/1999 | Maddox | 232/52 |
| 6,119,622 A | * | 9/2000 | Banerjea | 116/202 |
| 6,244,505 B1 | * | 6/2001 | Grimes et al. | 232/47 |
| 6,299,061 B1 | * | 10/2001 | Henson | 232/47 |

OTHER PUBLICATIONS

Astro Too Surplus Electronics, The Self–Decontaminating Mailbox, Dec. 26, 2001.*

* cited by examiner

Primary Examiner—William L Miller

(57) ABSTRACT

A mail box comprising a separated top and bottom port. A pivotally hinged gate/tray serves for depositing the incoming mail. The gate/tray has a pocket for outgoing mail and secures the top port from theft. Under the gate-tray a fixture with short wave ultraviolet (UV) light irradiates the box inside simultaneously generating ozone for a predetermined time. This time starts after the outgoing mail is put in the pocket or the incoming mail is dropped inside. A specially designed basket provides space around the mail where sanitizing gas freely diffuses. The light source can irradiate and activate gas-releasing material generating other disinfecting gas such as chlorine dioxide or ethylene oxide. The bottom port is closed by a locked door and allows for retrieving the mail, and setting and maintaining the UV-fixture. Two signals on an outside flag indicate the beginning and the end of the sanitizing process.

2 Claims, 4 Drawing Sheets

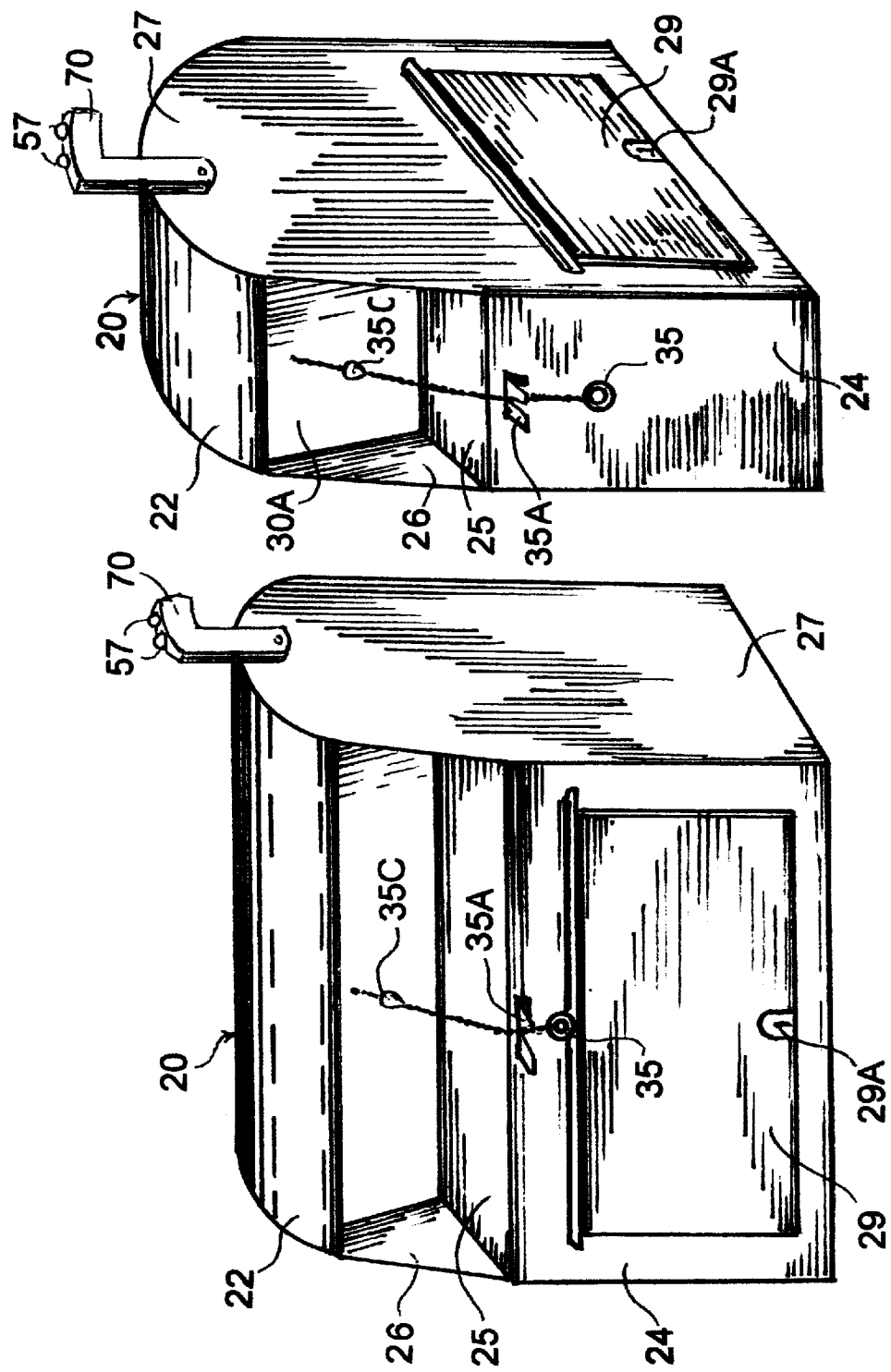

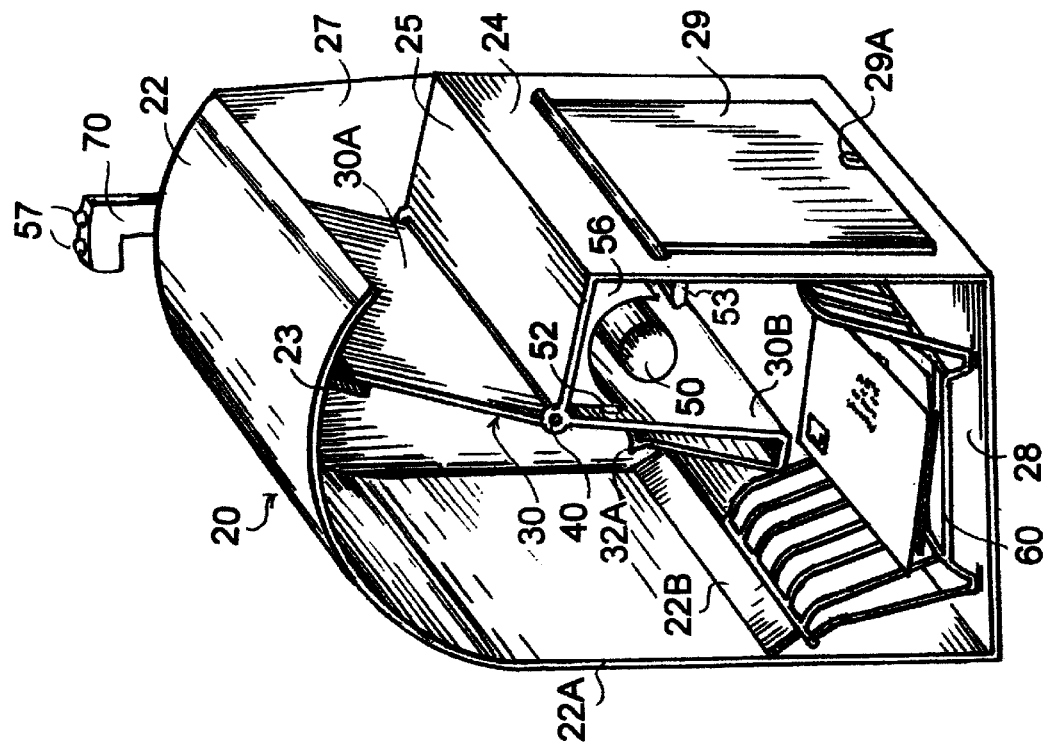
*FIG 2-A*
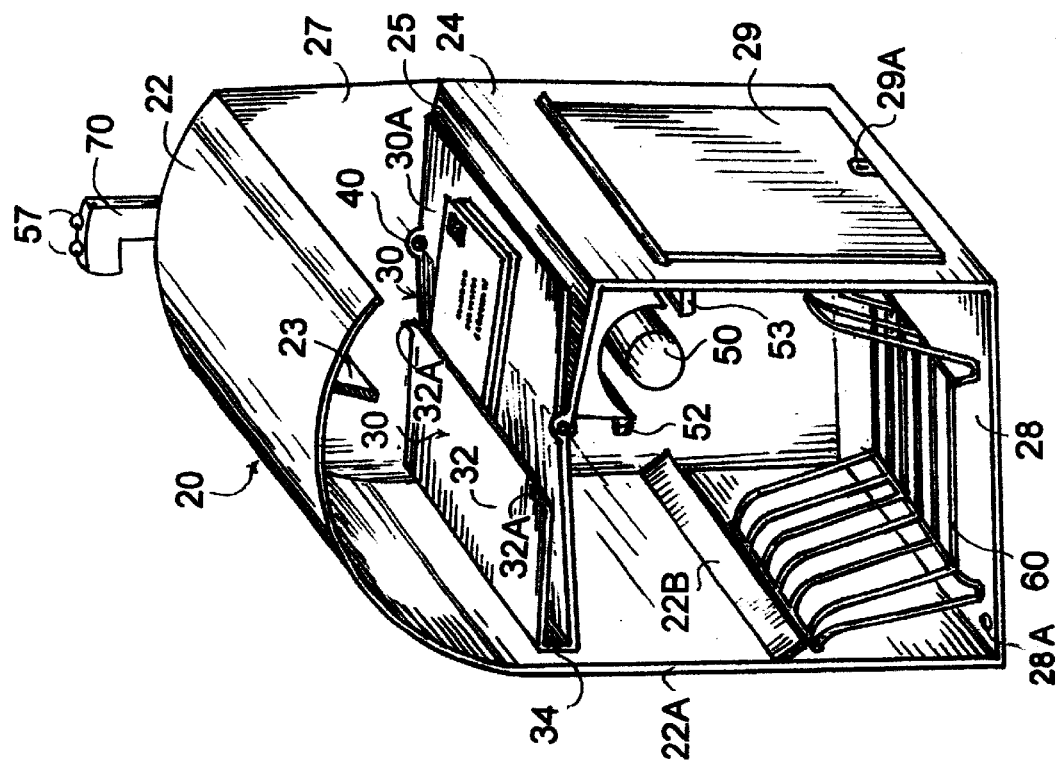
*FIG 2-B*

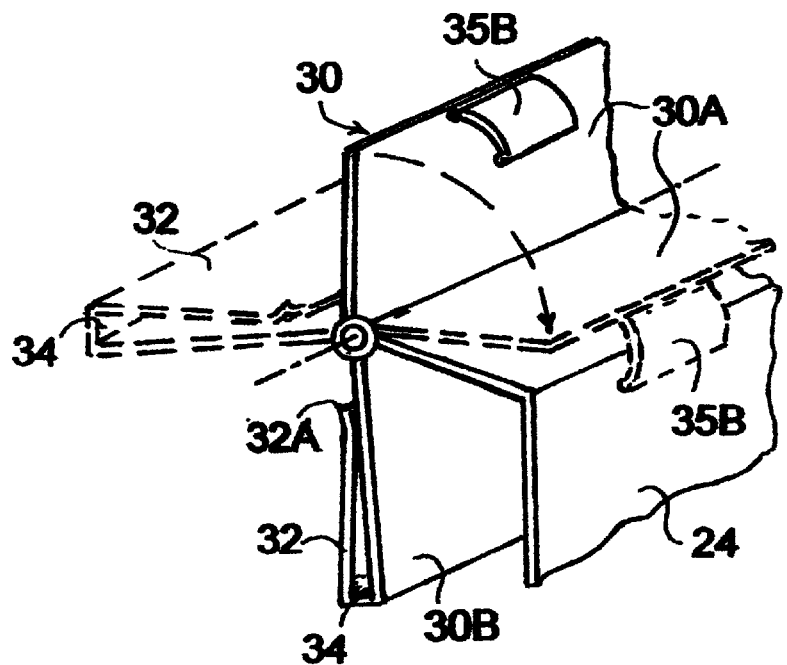
FIG. 3-A
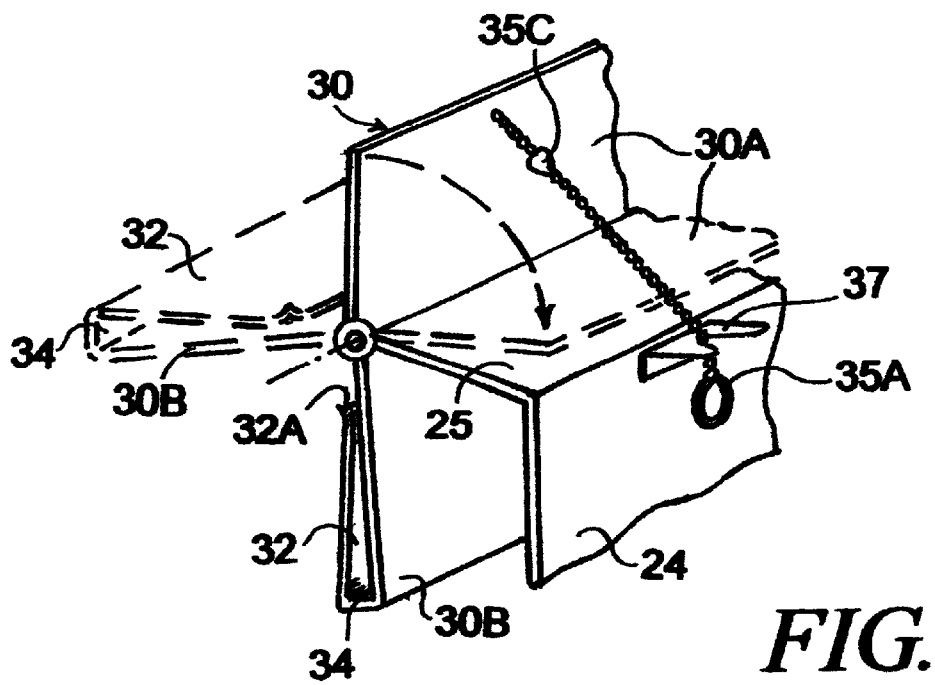
FIG. 3-B

SANITIZING SECURE AND SAFE MAIL BOX

BACKGROUND OF THE INVENTION

1. Field of the Invention

The present invention relates to the field of mail boxes, more specifically to the secured and safe mail boxes and further particularly to the sanitizing mail boxes.

2. Description of the Prior Art

The notion of secured mail box is the driving force for the variety of mail boxes. Taking apart the constructions in which the security locking device is used, because of their obviousness, one common approach is to use constructions applying two separate housings divided by secured moving part or space as in the following U.S. Pat. Nos. 827,482; 830,231; 1,202,251; 1,432,843; 2,602,584; 3,735,919; 5,000,378; 5,148,947; 5,938,113; 6,247,642.

The use of the means resembling revolving door as security closing door is in the base of U.S. Pat. Nos. 830,231; 5,482,208; 5,938,113; 6,247,642. This usage leads to constructions providing needed security, but not always adequate. Even in the most recent U.S. Pat. No. 6,247,642 of Wilson L. the solution for outgoing mail is mentioned only as wish, rather than designed as a construction.

Although the safety of the mail from the influence of the elements should be always the center of attention, but it has not been particular matter in the prior art. Most of the inventions consider those problems solved by the virtue of the concept of closed box. Cascading water, melting snow or condensation of water vapors inside of the box can readily have some negative consequences according to different designs of above mentioned inventions as well as in most of the mail boxes recently marketed.

Whereas a lot of diseases could be spread by bacteria-contaminated surfaces including mail of any kind, non of the prior art inventions relates to sanitizing mailbox for the incoming and outgoing mail by use of any means. On the other hand there are known devices for sanitizing the air flow such as U.S. Pat. Nos. 4,227,446; 5,523,057; 5,558,158; 5,635,133; 5,656,242 although non of them is providing sanitizing of a surface of object, more specifically surface of mail.

A main objective of the present invention is to provide a mail box having a sanitizing capabilities, whereby eliminating or drastically decreasing the effect of possible presence of bacteria, viruses or spores on the surface of the incoming and outgoing mail.

Another objective of the present invention is to ensure security of the incoming mail until it is retrieved from the owner.

Objective of the present invention is also to prevent the mail from any influence of the elements and their side effects as water condensation on inside surfaces.

Yet another objective of the present invention is to furnish the necessary level of safety to the user accomplishing aforementioned objectives.

SUMMARY OF THE INVENTION

According to the set heretofore objectives the present inventions includes a box with two main ports—one mounted in the top part of the box closed with horizontally pivoted self closing gate/tray for incoming/outgoing mail and another one in the bottom part closed with secured door for mail retrieving. The top part of the box is furnished with means for generating short wave ultraviolet light (UV-light) and respectively ozone whereby both of those agents act as sanitizers over the surface and even deeper into the mail. The bottom part of the box is provided with basket allowing direct exposure of the mail to the UV-light and by convection and diffusion free exposure to the ozone generated by the UV-source. The basket is designed to assure a distance between mail dropped and all inside of the box walls. As set heretofore the box secure the incoming mail by self-closing gate pivoted horizontally and providing limited angle of rotation. The gate is hinged to the box body along the main axis of rotation. The main axis of gate rotation is coaxial to the cylindrical shaped hood covering the gate and forming a small gap around the rotated gate. This construction do not allows the mail once dropped, to be retrieved from the same port. The inside portion of the gate has a pocket for the outgoing mail shaped as hard-core book cover and providing "closed" position when is empty and gradually opening upon the quantity of the outgoing mail. When the pocket is in "closed" position and horizontal, the top surface of the gate/tray is flat. This position of the gate/tray is considered "open box" position and the gate/tray is ready to be used as ingoing mail support. When moving the gate to vertical position, the mail slides from the surface of the gate/tray into grid or net type structure of the basket. The basket is design the way to provide a distinct distance from the bottom surface of the box and to assure air gap wrapping the entire pail of mail.

Further in accordance with the set objectives, inside the box there is a source of UV-light with wave length approximately 254 nanometers. The light source could be rechargeable battery supplied, or permanently wired to AC source through safety electric supplier. The light is directed onto the surface of the dropped mail which provides direct extinction of the surface bacteria, viruses and spores. The UV-light also produces ozone known as very strong disinfector over a certain concentration and which concentration can be easily achieved in the confined space of the box. The generated ozone diffuses into the air surrounding the mail destroying mentioned biological hazard. The coefficient of diffusion of the ozone is high enough to allow penetration even through paper material and to act as a disinfector even inside the enveloped mail. The heat generated from the UV-lamp prevents water from condensation when the incoming mail is colder than air in the boxed space until the temperature of the air and the mail equilibrates. The working time of UV-lamp can be regulated by different means such as preset time relay, preset electromechanical clock mechanism or similar. Those means are activated by contact switch when the mail is dropped into the box and the gate/tray get fixed in "closed box" position. The space between the bottom of the box and the mail over the grid or net, prevents the mail from eventual contact with any water collected on the bottom by previous condensation or blown by the wind as snow or rain. The bottom surface of the box is slightly sloped to one end where eventually collected water could be drained by small opening, closed most of the time with appropriate means.

BRIEF DESCRIPTION OF THE DRAWINGS

FIGS. 1-A,B are perspective view of the secured safe sanitizing mail box of the present invention having retrieving door at the front FIG. 1-A or at one of the side walls FIG. 1-B;

FIGS. 2-A,B are cross-sectional perspective view of the box thereof showing the two main positions of the pocket/gate charged with outgoing FIG. 2-A and incoming FIG. 2-B mail;

FIGS. 3-A,B are perspective view of two different types of means for one hand opening and fixing in charging/discharging positions of the gate/tray.

REFERENCE NUMERALS

Figure 4:
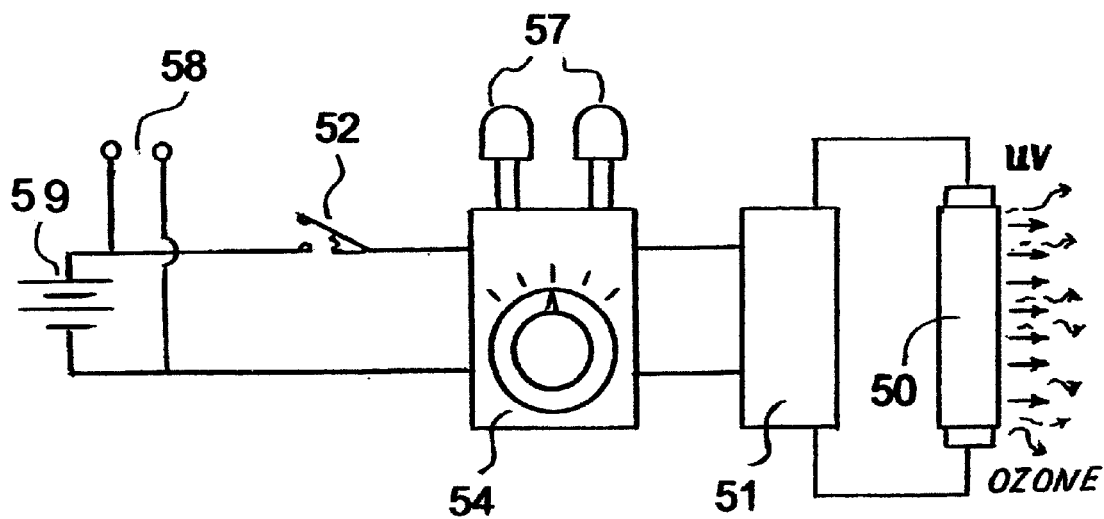
FIG. 4 is a schematic diagram of the electrical supply to UV-source and means of information for "start" and "end" of sanitizing procedure.

20. Security safety sanitizing mail box
22. Top cylindrical hood of the box
22A. Back wall—extension of the top hood
22B. Cascading lip on the inside of the back wall
23. Positioning frame or stopper on the inlet port
24. Front wall
25. Front hood-wall
26. Left side-wall
27. Right side-wall
28. Bottom of the box
28A. Means for draining the condensed water with plug
29. Door for retrieving the received mail
29A. Means for locking the door
30. Self closing mail gate/tray with means for fixation of the outgoing mail (hard-core-looking ongoing mail pocket)
30A. Front (visible) part of the gate/tray
30B. Back (hidden) part of the gate/tray
32. Top closing means (page, bracket, etc.) of the outgoing mail pocket
32A. Means for opening the outgoing mail pocket
34. Spine of the outgoing mail pocket
35. Means for forward opening of the gate/tray
35A. Means for fixation of the gate/tray in charging/discharging position
35B. Handle. Handle with magnetic means for fixation on the front wall
35C. Wider member on the rope/chain for fixation the gate in open position
37. Stopper plate for fixing the member 35C in open position
40. Hinge on the main axis of the gate/tray with mail pocket
50. Source of ultraviolet light (UV-lamp)
51. Transverter
52. Means for activation of the UV-source (button/switch)
53. Holder with sanitizing gas-releasing material
54. Means for regulating the length of the time activation for the UV-source
56. Means for fixing the UV source, transverter, time relay and reflector in overlooking position
57. Means for observation of the duration of activation time and its finish-photodiodes (for example: red—sanitizing activated/green—collect the mail)
58. External source of power supply
59. Internal source of power supply
60. Means to keep the incoming mail out of contact with the mail box walls;
    Same means allowing to retrieve the mail from the mail box (mail basket)
70. Info-flag handle with places for photodiodes

DETAILED DESCRIPTION OF THE INVENTION

One main embodiment in two different variations is shown and explained on FIGS. 1 to 4. As far as both of the variations have the same aim and are functioning the same way both of the variations are shown in parallel. Parts having the same main function are numbered the same way in all drawings.

As seen on FIGS. 1-A,B and FIGS. 2-A,B, the mail box 20 of the present invention is cylindrically hooded secluded box with top port for depositing outgoing and incoming mail and bottom port for retrieving the received mail.

As seen on FIGS. 1-A,B the top port of the mail box 20 is fully closed by the means of top gate/tray 30A and have a retrieving door 29 normally closing the bottom port with means 29A for locking the door to the box. The bottom port closing door is mounted on box front side FIG. 1-A or left/right side FIG. 1-B. It is hanged preferably along its top side, thereby to prevent the box from snow or rain when opened. The box top side is shaped as cylindrical hood 22 which extends partially forward as overhang to prevent the top port and gate/tray 30A from snow or rain. The cylindrical hood 22 extends as vertical back wall 22A of the box 20 adjacent to the bottom wall 28 which is further adjacent to the front wall 24, seen on FIGS. 2-A,B. The top part of the front wall 24 is bent backward forming a sloped wall 25 and preferably have the hinge 40 mounted along its inner edge. The hinge 40 could be replaced by two hinged rivets, as shown on FIGS. 2-A,B. Parallel to the main axis of the cylindrical hood 22 is pivotally hinged the rectangular shaped gate/tray 30 which is closing the top port of the box and which gate/tray is restricted in its rotation to the "closed" position by means of positioning stopper or frame 23, at in its "open" position by the front sloped wall 25.

The axis of hinge 40 divides the gate/tray 30 in two parts—front or visible part 30A, normally closing the mail box, and its back hidden part 30B inserted into the box 20 and longer inward than front part 30A, seen on FIGS. 2-A,B and FIGS. 3-A,B. Part 30B which is entirely inside of the box is forming a book's hard-cover-like pocket for the outgoing mail by means of the spine 34 adjacent to the back edge of the gate/tray and page 32 adjacent to the other side of the spine 34 and covering the back part 30B of the gate/tray. One or two corners 32A of the page 32 close to the main axis are slightly open up and allow the outgoing mail to be inserted easily into the pocket. The thickness of the pocket and its capacity depends on the width of the spine 34, but should not exceed ¾ of the opening of the incoming port. There is an angle between front part 30A and inserted part 30B of the gate/tray 30 as the surface 30B is bent down along the hinge/axis 40 well seen on FIGS. 2-A,B and FIGS. 3-A,B. The purpose of this bent is to provide a pocket with enough volume and respective capacity for outgoing mail. The other purpose of this bent is to provide flat surface of the gate/tray 30 when page 32 is closed (the outgoing mail is retrieved) and incoming mail have to be charged on the gate/tray 30. When the pocket of the gate/tray is closed the surface of the page 32 have to represent an extension of the plane formed by surface 30A. It is understandable that by enlarging the width of spine 34 the bent of gate/tray must be deeper thereby to keep always flat the entire working surface of the gate/tray for incoming mail, seen on FIGS. 3-A,B.

As shown better on FIGS. 2-A,B when in "closed" position the gate/tray 30 is forming internal hooded space secluded on one side from the back gate/tray 30B, on the top from the sloped front wall 25 and on the third side by the front wall 24. The other two side walls 26 and 27 of the box are defining this hooded space on the top part of which is fixed ultraviolet light source 50 with wave length pick at 254 nanometers or similar. The UV-source is mounted in a fixture 56 including other electrical parts and means, shown on FIG. 4, to provide appropriate UV-light with power such as: internal source of power supply 59, transverter 51, time relay 54, reflector as well as parts for mechanical or magnetic fixation to the internal surface. On the bottom 28 of this hooded space is placed basket 60 for the incoming mail. The basket has its grid-type walls sloped inward touching the internal box surface only with the top edges of its walls. A legs situated preferably in the corners of the mail basket do not allow the incoming mail when dropped to touch the bottom of box 20. The bottom is slightly sloped to one of the side walls having in its lowest part means—small plugged opening 28A for draining eventually collected water. The basket 60 provides a full air gap wrapping the incoming mail suspended the in the mentioned hooded space. An optional holder with gas-releasing material 53 capable of generating sanitizing gas (such as chlorine dioxide, ethylene oxide or similar), when irradiated by light, can be placed close to the UV-source whereby to increase the disinfecting power of the box.

Function of the Preferred Embodiment

The source of short wave ultraviolet light is known to generate ozone in the air, in this case into the limited air volume of the mail box. When acting the UV-source is providing UV-radiation having direct bactericide (germicidal) effect. The UV-radiation is generating also proportional to the source power and time of its work concentration of ozone, which diffuses freely around the inserted mail. The present invention alleviates free diffusion of the ozone around the mail allowing it to be exposed to direct UV-light, seen on FIGS. 2-A,B. As the basket 60 has its side grids sloped to the inner side of the box walls, they provide needed distance for ozone to diffuse around, as well as the corner legs which provide space between the mail charged in the basket and the bottom 28 of the box. This way the mail is suspended and not contacting eventually condensed or cascaded water on the inner surface of the box and is fully wrapped in air with sufficient concentration of ozone when UV-source 50 is activated. The optional gas-release source 53 is activated for the time when UV-source irradiates the inner space of the box and releases another type sanitizing gas—chlorine dioxide, ethylene oxide or similar.

There are means to activate the UV-source when the gate/tray 30 is in "closed" position. Button/switch 52 is mounted on the source 50 holder/reflector 56 or on surface of the sloped wall 25. The button/switch 52 is pressed when gate/tray is completely closed by the gravity because the weight of gate/tray part 30B plus the weight of the spine 34 and page 32, is much bigger than the weight of the visible front part 30A, therefore the pocket on the gate/tray 30 is inclined to rotate the gate always into "closed" position, seen on FIGS. 2-A,B. Once activated the UV-source 50 generates UV-light and ozone for the predetermined time (preferably over 0.5 hour) by the means of timing relay assembly 54 as shown on FIG. 4. The time of activation is indicated by LED indicators 57 mounted on the information flag 70 (preferably red colored for active UV and green colored when the mail can be collected). The electric supply for the UV-source could be based on build in or rechargeable battery 59, or permanent DC supply 58 by external source. For safety reason DC supply up to 6–9 volts could be separated from the mail box.

On FIGS. 1-A,B two variants of the present invention are shown. The variant on FIG. 1-B is designed for standard envelopes and wraps to be introduced lengthwise on the gate/tray. The variant on FIG. 1-A is more convenient for bigger envelopes and packages to be introduced widthwise on the gate/tray.

In both cases the gate/tray serve as self closing door securing at the same time the dropped mail from theft.

In both variants the means for "one hand" service for incoming and outgoing mail are used as shown on FIGS. 3-A,B. Those means provide temporary fixation of the gate/tray in "open" position. They can be based on magnetic fixed lock FIG. 3-A or chain with means for temporary fixation FIG. 3-B.

Materials

No open metal surfaces have to be used all over the inside of the box 20. The ozone has tendency to recombine its atoms on metal surfaces forming three molecules of oxygen from every two molecules of ozone. The presence of open metal surface can deplete completely ozone concentration. On the other hand ozone is strong oxidizer and can contribute to the corrosion on open metal surfaces.

All materials used inside the box of the present invention must be UV and ozone resistant. Well suited are plastic coated metal surfaces as well as plastics recommended for outdoor use—modified PVC, modified acrylic, polyurethane, polycarbonates etc.

As UV-source any light source known as germicidal lamp dimensionally suitable could be used, but lamps with low consumption designed for portable units and use such as types G4T5, G6T5, G8T5 are preferable. A standard or market available electric transverter, usually coming as a part of the portable unit's body, is the power source directly supplying the UV-lamp. For convenience the time relay, determining the activation time for the UV-source and the transverter, are preferably combined in one body.

Safety

The ozone is a gas with specific odor—three atoms molecule modification of the oxygen which is not very stable and tend to form oxygen allowing one atom of free oxygen which is extremely active either to recombine with another atom oxygen to oxygen gas molecule or to oxidize rapidly many other materials including biological objects. Those properties are the base of the use of ozone as powerful germicidal gas destroying bacteria, spores and viruses of different origin. The ozone is a natural part of the ambient ground-close atmosphere and its concentration varies in large scale (compare to other atmosphere gases), range from 10 to 60 ppb. A small concentration of ozone is considered healthful as a natural sanitizing agent.

The ozone concentration achievable in the safety box is about 2–5 ppm after 0.5 hr activation of the UV-source. Even if the mail box is opened immediately after such level is achieved, the concentration will drop instantly several hundred times for a few seconds, because of the big diffusion coefficient of the ozone, big door opening and high volume of surrounding air—thousands times overwhelming the box volume and providing extremely high gradient of concentration depletion.

The amount of ozone generated and immediately diluted to the normal atmosphere concentration is negligible even assuming simultaneous work of millions sources alike. Therefore the sanitizing mail box can be considered as environmental friendly device.

It should be understood that it is in the spirit of the present invention to provide a mail box with sanitizing means by generating short wave UV-radiation and ozone simultaneously and to wrap in this atmosphere any mail for the time considerable enough to extinct all microorganisms and spores. At the same time the box upon the present invention is providing secured space for the incoming mail and means for one hand operation to drop the incoming mail and/or pick up the outgoing mail. The box is secured from theft and influence by the elements—rain, snow, cascading water, ice etc.

What we claim is:

1. A secure mail box comprising: a top port and a bottom port; a horizontal pivotal gate with a limited angle of rotation, said gate including a substantially flat front part and a back part shaped to define a pocket for holding outgoing mail; said top port normally closed by said front part of said gate and said bottom port normally closed by a door, said door including a locking means; a basket for receiving incoming mail dropped therein from said gate; a source of short wave UV light mounted in a fixture, said fixture including a means for reflecting said UV light; a means for electrically powering said source of UV light for a predetermined time; a means for activating said source of UV light when said top port is closed by said gate whereby to expose the mail within the mail box to UV radiation and simultaneously generated ozone; and a flag having two light indicators on a top surface thereof for indicating activation of said source of UV light and non-activation of said source of UV light.

2. The mail box of claim 1, wherein all inside surfaces of said box are made from or are covered by ozone compatible materials whereby said surfaces will not interfere with said generated ozone to cause recombination to oxygen or corrosion.

* * * * *